United States Patent [19]

Barker et al.

[11] Patent Number: 4,671,445

[45] Date of Patent: Jun. 9, 1987

[54] FLEXIBLE SURGICAL STAPLER ASSEMBLY

[75] Inventors: John M. Barker, Port Hueneme; Alan K. Plyley, Goleta, both of Calif.

[73] Assignee: Baxter Travenol Laboratories, Inc., Deerfield, Ill.

[21] Appl. No.: 639,163

[22] Filed: Aug. 9, 1984

[51] Int. Cl.[4] .................. A61B 17/00; A61B 17/11
[52] U.S. Cl. .................. 227/19; 227/141; 227/DIG. 1; 74/501 R
[58] Field of Search .................. 227/DIG. 1, 19, 141; 128/334 R, 227, DIG. 1 M, DIG. 1 T; 74/501 R, 502, 532

[56] References Cited

U.S. PATENT DOCUMENTS

| | | | |
|---|---|---|---|
| 2,531,740 | 11/1950 | Orscheln | 74/501 R |
| 4,304,236 | 12/1981 | Conta et al. | 128/325 |
| 4,473,077 | 9/1984 | Noiles et al. | 227/19 X |
| 4,485,817 | 12/1984 | Swiggett | 227/DIG. 1 X |
| 4,488,523 | 12/1984 | Shichman | 227/DIG. 1 X |
| 4,580,712 | 4/1986 | Green | 128/334 R X |
| 4,606,343 | 8/1986 | Conta et al. | 128/334 R X |
| 4,610,383 | 9/1986 | Rothfuss et al. | 128/334 R X |

FOREIGN PATENT DOCUMENTS

| | | |
|---|---|---|
| 0101310 | 2/1984 | European Pat. Off. . |
| 1057729 | 5/1959 | Fed. Rep. of Germany . |
| WO82/00968 | 4/1982 | PCT Int'l Appl. . |

Primary Examiner—Howard N. Goldberg
Assistant Examiner—Taylor J. Ross
Attorney, Agent, or Firm—Robert E. Hartenberger; Richard Meyers; Roger A. Williams

[57] ABSTRACT

A flexible surgical stapler assembly includes a staple firing head assembly and a handle actuator assembly connected to the staple firing head assembly through a flexible spine. The staple firing head assembly includes an anvil assembly defining an anvil surface which provides an array of staple forming depressions. A staple housing on the staple firing head assembly carries an array of staples to be formed. A staple pusher means on the staple firing head assembly is provided for exerting a force on the staples in the staple housing to eject the staples from the housing and form the staples against the anvil surface. The handle actuator assembly includes a housing which defines an inner cavity. A cable carrier is provided within the cavity and is freely slidable within the cavity. A length of flexible cable is connected at one of its ends to the cable carrier and at its other end to the anvil assembly of the staple firing head assembly. A trigger mechanism consisting of a lever is provided on the housing operatively connected to the cable carrier for moving the cable carrier and thereby concomitantly forcing the staples out of the staple housing to form the staples against the anvil surface.

32 Claims, 11 Drawing Figures

FLEXIBLE SURGICAL STAPLER ASSEMBLY

BACKGROUND OF THE INVENTION

The invention herein relates to a surgical stapler instrument and, more particularly, to a flexible surgical stapler instrument and assembly which consists of a staple firing head assembly and which is interconnected through a flexible coupling to a handle actuator assembly.

The field of surgical stapling has grown since its inception in the 1960's. During this time of growth, basically four different types of stapling instruments have developed. One type of stapling instrument is a skin stapling instrument used to close wounds on the skin. A second type of stapling instrument is a surgical stapling instrument which is used for inverted linar anastomosis or gastrointestinal anastomosis. Such an instrument is designed to provide a side by side connection of two lumens of organs. Such instruments generally include two double rows of staples with a cutting blade between the double rows.

Another common surgical instrument is a thoracic abdominal instrument which produces a linear suture line with a double staggered row of staples. Such an instrument generally consists of a C-shaped frame. A disposable anvil for forming the staples adapts to a fixed outer limb of the C of the instrument, and a disposable staple cartridge adapts to a corresponding inner limb of the C-shaped instrument.

Another surgical stapling instrument is an end to end anastomosis surgical stapling instrument. In such an instrument, the lumen of an organ is rejoined, such as, for example, two bowel segments are rejoined end to end. Such an instrument generally provides a double row of staples and a cutting blade. The double row of staples provide the means for connecting the lumens end to end while the cutting blade removes that portion of the organ extending inwardly of the lumen at the connection site.

In the surgical stapling instruments, there is a staple firing head and a handle assembly for firing the staples. Currently, such instruments include a mechanical linkage between the handle actuator and the staple firing head in order to fire the staples. In use, it is often difficult to position a stapling instrument in order to insure a proper and acceptable connection or joining of the tissue. This is often due to the differing locations where the stapling instrument is being used and where the joining of tissue is occurring. It would be desirable to provide stapling instruments which would have a stapling firing head assembly which could be readily positioned at the tissue site to be joined and which would provide flexibility between such stapling firing head and the handle actuator assembly. Such flexibility would also be desirable on an end to end anastomosis instrument as it would allow insertion of the staple firing head or flexible connector through tortuous passages of an organ such as the sigmoid colon.

SUMMARY OF THE INVENTION

The invention herein is directed to a flexible surgical stapling assembly which includes a staple firing head assembly which is flexibly interconnected to a handle actuator assembly. More particularly, the flexible surgical stapler assembly herein is directed to a staple firing head assembly which is connected to a handle actuator assembly through a length of flexible cable which permits the staple firing head assembly to be readily positioned regardless of the orientation of the handle actuator assembly.

Another feature of the flexible surgical stapler assembly herein is that the handle actuator assembly can be used with a variety of staple firing head assemblies. That is, for example, the handle actuator assembly of the flexible surgical stapler assembly herein can be used with a thoracic abdominal staple firing head assembly and with an end to end anastomosis head assembly.

The flexible surgical stapler assembly herein includes a staple firing head assembly connected through a length of flexible cable to a handle actuator assembly. The staple firing head assembly includes an anvil assembly defining an anvil surface which provides an array of staple forming depressions. The anvil assembly can be a disposable anvil which is mounted on the staple firing head assembly. The staple firing head assembly also includes a staple housing which carries an array of staples. The staple housing can be a disposable staple cartridge which can be inserted in the staple firing head assembly. The anvil assembly is spaced from the staple housing assembly by a gap sufficient for receiving the tissue to be stapled. The anvil/staple housing gap can be controlled via a knob located at the end of the handle actuator assembly to provide an adjustment for differing thickness of tissues. The staples can be provided in any array depending on the end use of the surgical stapler assembly. A staple pusher is also provided in the staple firing head assembly. The staple pusher cooperates with the staple housing and aligns with the staples in the housing. Upon actuation of the stapler instrument, the staple pusher exerts a force on the staples or on staple drivers in the staple housing to remove the staples from the staple housing and to form the staples against the depressions in the anvil surface.

The handle actuator assembly includes a housing which defines an inner chamber. A cable carrier is slidable within the inner chamber or cavity. A length of flexible cable is connected at one of its ends to the cable carrier. The remaining end of the length of the flexible cable is connected to the anvil assembly of the staple firing head assembly. A handle is provided on the housing of the handle actuator assembly. The handle is operatively connected or connectable to the cable carrier for moving the cable carrier and thereby the cable to concomitantly force the staples out of the staple housing and form the staples against the depressions on the anvil surface.

The flexible surgical stapler assembly herein primarily consists of a handle actuator assembly which includes a cable carrier attached to a length of flexible cable and a handle which can be connected to the cable carrier for moving the cable carrier and cable relative to the handle actuator assembly. The remaining end of the cable is attached to the anvil assembly in the staple firing head assembly. As the handle is depressed to move the cable carrier, it also moves the cable. As the cable moves, it also moves the anvil. It should also be noted that as the tissue is approximated between the anvil assembly and staple housing assembly by rotation of the knob on the handle actuator assembly, the cable and anvil move due to the rotation of the knob. The anvil moves toward the staple housing which is positioned between the anvil and handle actuator assembly. As the anvil moves toward the staple housing, the anvil assembly exerts a force on the staple housing and it begins to move both the anvil and staple housing toward the staple pusher which generally remains fixed relative to the staple housing, anvil and cable. As the anvil and staple housing continue to advance toward the staple pusher, the staple pusher encounters the staples (or staple drivers) within the staple housing, thereby causing the anvil and staple housing to advance relative to the staples which, upon encountering the anvil, form against the depressions on the anvil surface.

BRIEF DESCRIPTION OF THE DRAWINGS

The particular advantages and details of the present invention will become more evident from a consideration of the following detailed description when reviewed in combination with the appended drawings wherein.

DETAILED DESCRIPTION

Figure 1:
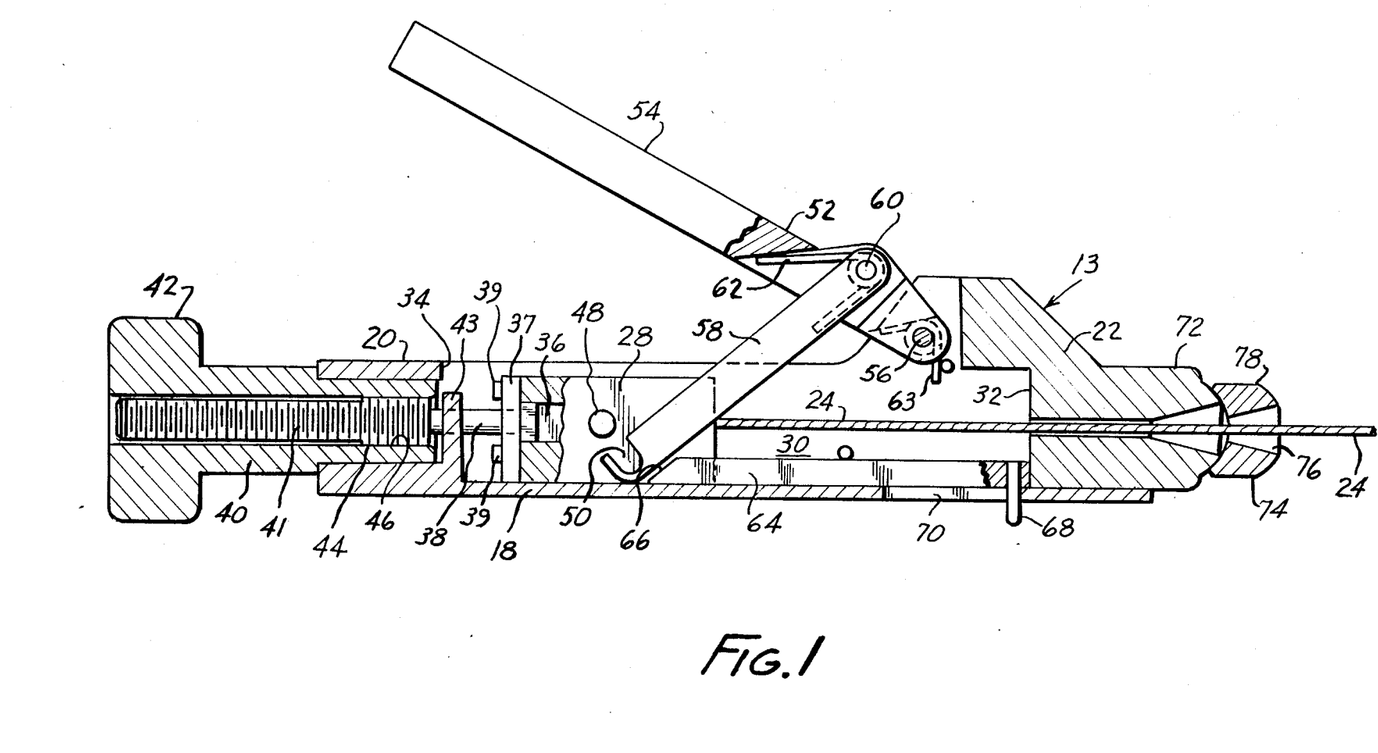
FIG. 1 is a side elevational view partially in cross section of an embodiment of a handle actuator assembly for a flexible surgical stapling assembly herein.
Figure 2:
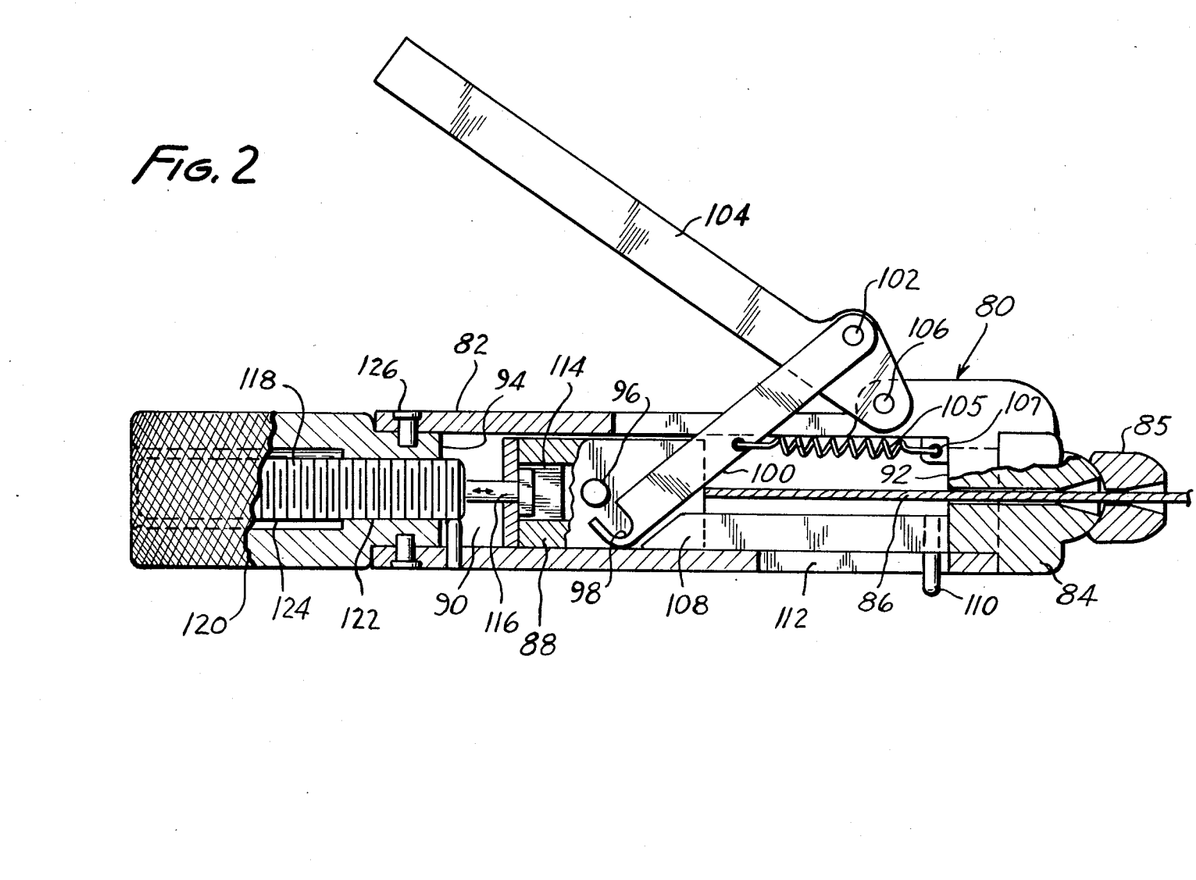
FIG. 2 is a side elevational view partially in cross section of a preferred embodiment of a handle actuator assembly for use in the flexible surgical stapling assembly herein.
Figures 3, 3A:
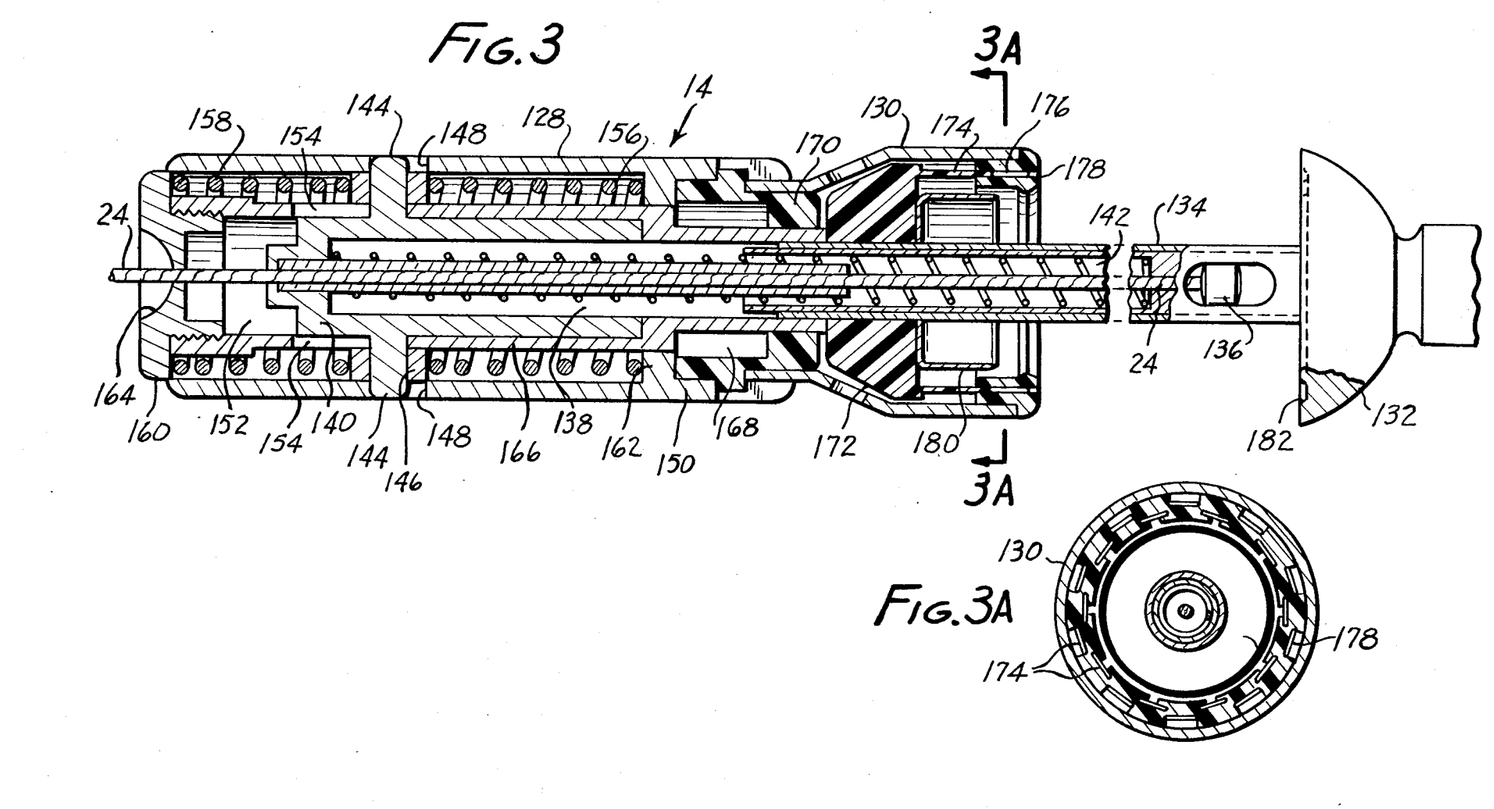
FIG. 3 is a side elevational view partially in cross section of an embodiment of a staple firing head assembly for use in end to end anastomosis.
FIG. 3A is an end view of the staple firing head assembly taken along line 3A of FIG. 3.
Figure 8:
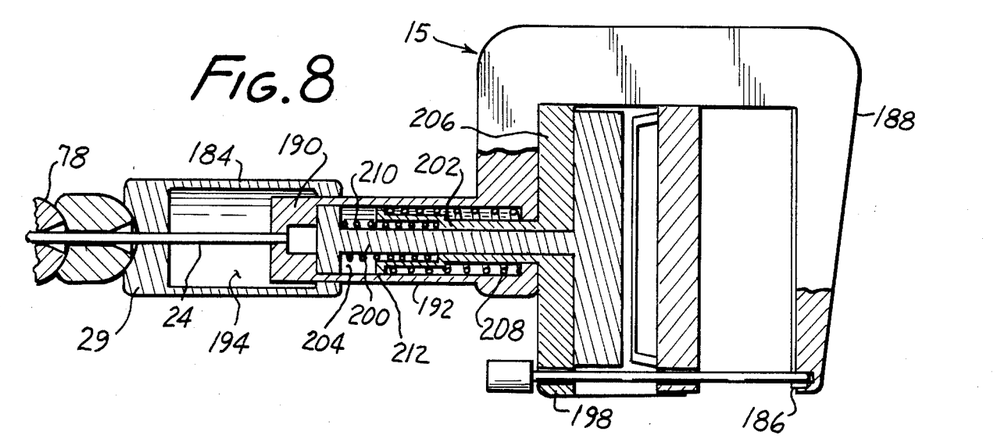
FIG. 8 is a side elevational view partially in cross section of a staple firing head assembly for use in providing linear extending staples.
Figure 9:
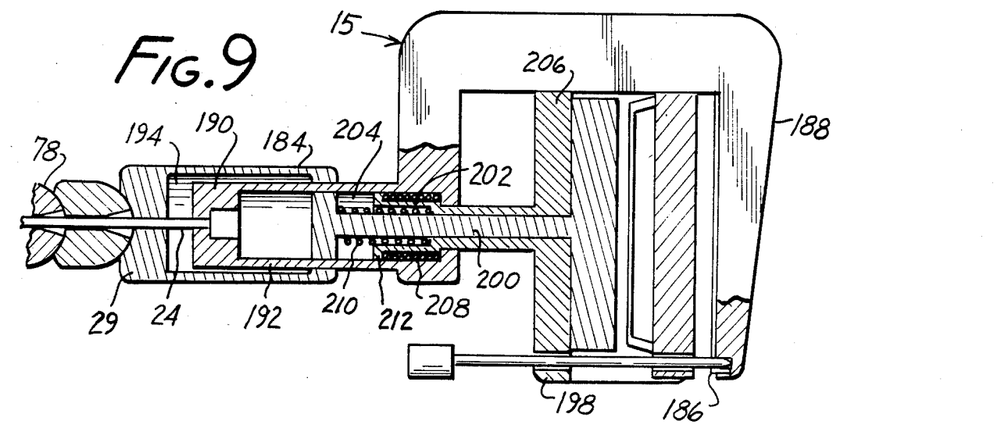
FIG. 9 is a side elevational view partially in cross section of the staple firing head assembly shown in FIG. 8 illustrating the approximation of tissue between the anvil and staple housing.
Figure 10:
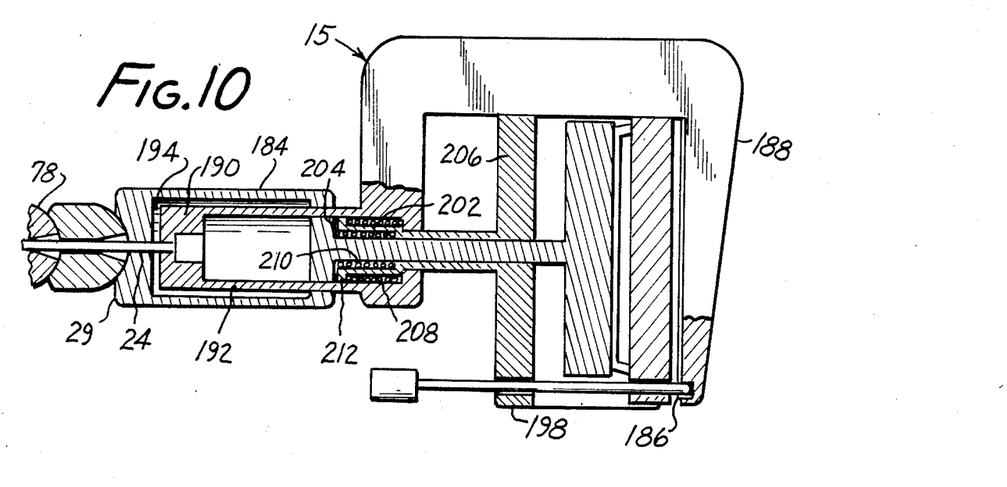
FIG. 10 is another side elevational view partially in cross section of the staple firing head assembly of FIG. 8 showing the head assembly as the staples have been fired from such head assembly.

The flexible surgical stapler instrument assembly herein will be described with regard to the accompanying drawings. In particular, FIGS. 1 and 2 illustrate two working embodiments of a handle actuator assembly. FIG. 3 illustrates a stapling head assembly for use in end to end anastomosis and FIGS. 4–7 schematically represent the operation of such an end to end anastomosis flexible stapling instrument assembly. The remaining FIGS. 8–10 represent a linear stapling head assembly and its operation.

Figure 4:
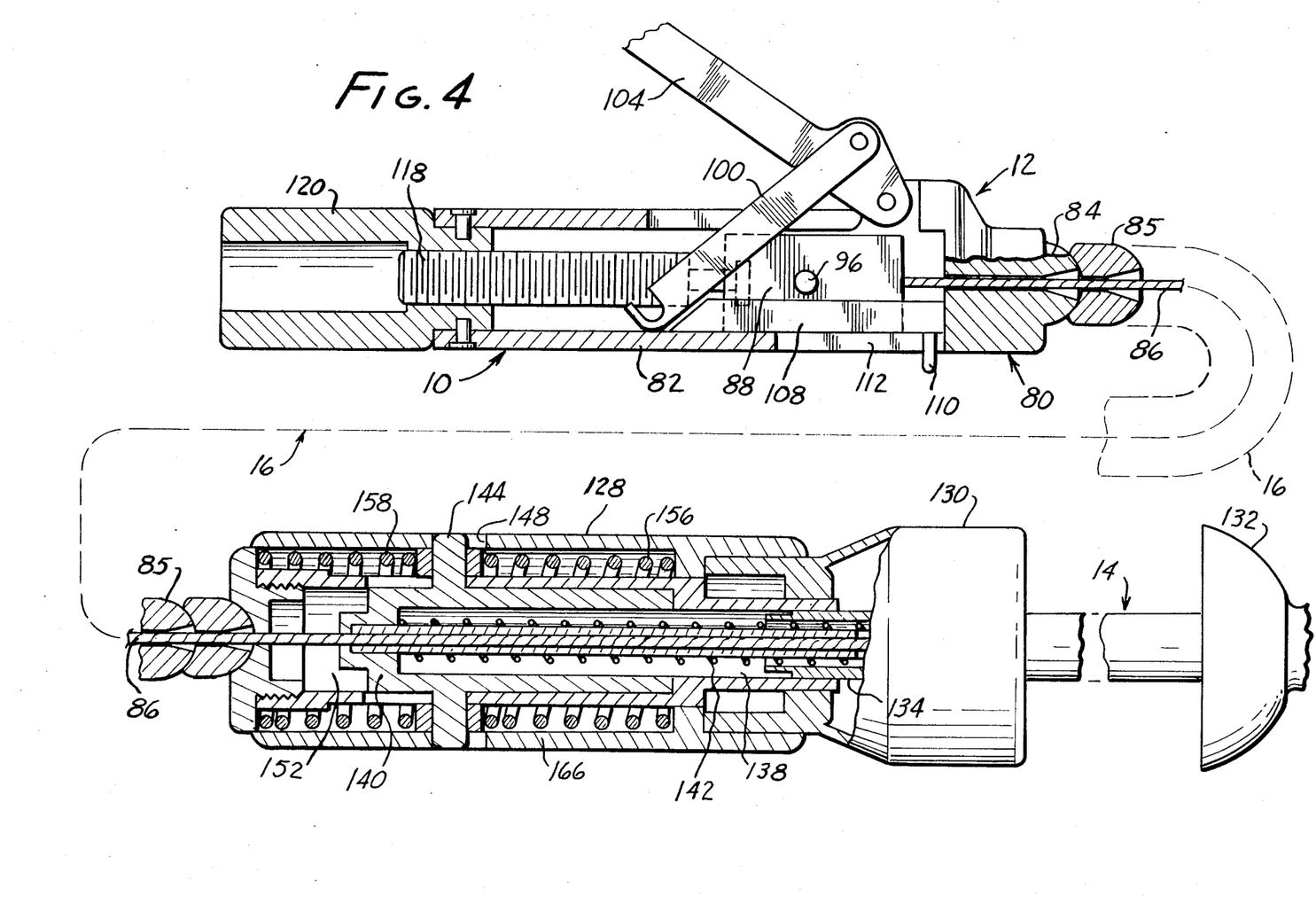
FIG. 4 is a side elevational view partially in cross section of an embodiment of an end to end anastomosis flexible stapling instrument assembly herein illustrating the location of the actuation elements in the assembly prior to use.

The flexible stapler instrument assembly herein is best illustrated with regard to FIG. 4 which shows the flexible stapler instrument assembly 10. The flexible stapler instrument assembly includes three sections, namely, a handle actuator assembly 12, a stapling head assembly 14, and a flexible spine assembly 16 interconnecting the handle actuator assembly and stapling head assembly.

In order to facilitate the description of the assembly herein, the description will first be directed to the handle actuator assembly and, in particular, to a handle actuator assembly 13 shown in FIG. 1. The handle actuator assembly therein includes a housing 18 which can be constructed of any suitable material and have any geometric configuration. For example, the housing can be a generally tubular housing having a length greater than its width and can be either cylindrical or multi-sided tubular. The housing can be constructed of any suitable material, and acceptable materials include stainless steel and various medical grade plastics. The handle assembly can be constructed of metal to provide a reusable handle assembly and can be constructed of plastics to provide a disposable handle assembly. When the handle actuator assembly is constructed so as to be disposable, the entire flexible stapling instrument assembly can also be constructed so as to be disposable.

The housing 18 includes a rear spacer 20 and a front spacer 22 which combine with the housing to define a cavity 30 within the housing. A cable carrier 28 is positioned within the cavity. The cable carrier is freely slidable within the cavity of the housing.

A cable 24 extends through and from the front spacer 22. The cable 24 can be any suitable cable and is preferably a multi-stranded steel wire cable. The cable is attached at one of its ends to the cable carrier 28.

The cable carrier is freely slidable within the cavity 30 of the housing. The cable carrier can move between the end wall 32 of the front spacer and the end wall 34 of the rear spacer. The cable carrier is keyed to the housing to prevent rotation and to define a race in which the cable carrier can slide. The length of movement of the cable carrier depends upon the stapling head assembly attached at the other end of the cable. The staple carrier includes a cavity or recess 36. The recess 36 is adapted to receive a connecting rod 38 which is interconnected to a threaded shaft 41. The recess 36 can be enclosed by a plate 37 which can be joined to the cable carrier by suitable bolts 39.

The threaded shaft 41 is part of a gap adjustment assembly 40 which is keyed to the housing or the rear spacer of the housing. The gap adjustment assembly permits the approximation of the tissue to be stapled between the anvil surface and the staple housing prior to the firing of the staples. The gap adjustment assembly includes the threaded shaft 41 which is adapted to move longitudinally within the housing. The threaded shaft 41 has an outer threaded surface 46 which engages a threaded surface 44 on an inner surface of a rotatable knob 42. The rotatable knob 42 rotates within the housing but does not move in or out of the housing, that is, does not move its position relative to the housing except for rotation. The threaded shaft 41 is keyed to the housing along the same key as the cable carrier such that the threaded shaft does not rotate. The threaded shaft can be prevented from rotating by a radial protrusion 43 through which the threaded shaft can move or which can move concomitantly with the threaded shaft in the cavity 30. Since the threaded shaft 41 does not rotate, it moves inwardly and outwardly of the housing as the rotatable knob 42 is rotated. The threads on the rotatable knob interlock with the threads on the threaded shaft and, upon rotation of the knob, move the threaded shaft. Concomitantly with the movement of the threaded shaft, the cable carrier 28 moves due to the attachment of the cable carrier to the threaded shaft through the connecting rod 38. The function of the rotatable knob and threaded shaft 41 will hereinafter be described with regard to the description of the stapling head assembly and overall operation of the instrument.

Also on the housing 18 is a lever assembly 52. The lever assembly provides a trigger mechanism for firing the staples and forming the staples. The lever assembly 52 includes a lever 54 which is pivotally attached to the housing through a pivot pin 56. The lever 54 is also pivotally attached to an arm 58 through a second pivot pin 60. A first torsion spring 62 can bias the lever 54 against the arm 58 and can wrap around the second pivot pin 60 and a second torsion spring 63 can bias the lever 54 against the housing and can wrap around the first pivot pin 56. The second pivot pin 60 provides a pivotal linkage which, upon movement of the lever 54 toward the housing, causes the arm 58 to move toward the rotatable knob or rearward end of the housing.

The cable carrier 28 is provided with an outwardly extending pin 48. The outwardly extending pin 48 is designed to engage a corresponding slot 50 on the arm 58. As can be seen in FIG. 1, the arm 58 is initially not engaged with the pin 48 on the cable carrier. Such an arrangement provides for movement of the cable carrier without moving the triggering mechanism in the lever assembly 52.

To engage the slot 50 of the arm 58 with the pin 48 on the cable carrier, a ramp 64 is provided in the cavity 30 of the housing. The ramp 64 is freely slidable within the cavity. The ramp has a leading end which includes a sloped surface 66 which engages the slotted end of the arm 58 and moves such slotted end toward the pin 48 on the cable carrier. The ramp 64 includes an extending pin 68 which extends outwardly from the cavity and projects through a slot 70 on the housing. The extending pin 68 provides the ability to manually move the ramp from a first position wherein it does not engage the slotted end of the arm 58 to a second position whereby the ramp engages the slotted end and concomitantly engages the pin 48 on the cable carrier with the slot 50 on the arm.

The forward surface of the front spacer 22 is a hemispherically-shaped surface adapted to mate with a spine segment 74. The spine segment 74 extends around the cable and protects the cable while permitting flexibility of the cable and positionability of the stapling head assembly remote from the handle actuator assembly. A plurality of spine segments extend around the cable between the handle actuator assembly and the stapling head assembly. Each of the spine segments 74 includes a cylindrical lumen 76 which as its forward end opens into a conical lumen. The forward facing surface of each spine segment is a hemispherically-shaped surface 78. The rearwardly facing surface of each spine segment is a hemispherically-shaped concave recess which is adapted to mate and coincide with the hemispherically-shaped forward surface of the adjacent spine segment. The spine segments abut one another and extend between the handle actuator assembly and stapling head assembly and translate a force which maintains that portion of the staple firing head assembly to which the forwardmost spine segment abuts in a fixed position relative to the cable. The operation will be hereinafter described with regard to the operation of the overall flexible stapling instrument assembly.

With regard to FIG. 2, a preferred embodiment of a handle actuator assembly 80 is illustrated. Basically, the handle actuator assembly 80 shown in FIG. 2 is similar to the handle actuator assembly 13 shown in FIG. 1. The two handle actuator assemblies primarily differ in their gap adjustment assemblies.

The handle actuator assembly 80 shown in FIG. 2 includes a housing 82. The housing includes a front spacer 84 which includes a hemispherically-shaped forward surface adapted to mate with a spine segment 85.

The housing defines a cavity 90 in which rides a cable carrier 88. The cable carrier 88 is freely slidable along a provided race between the forward end wall 92 and the rearward end wall 94 of the cavity in the housing. The cable carrier is attached to a cable 86 which extends through the forward end, front spacer, and spine segments.

The cable carrier includes an outwardly extending pin 96 which is designed to engage and cooperate with a slot 98 on an arm 100 which is pivotally connected through a pivot pin 102 to a lever 104 which in turn is pivotally linked through a pivot pin 106 to the housing. The arm 100 can be spring biased against the housing through a coil spring 105. Such a biasing coil spring 105 maintains a tension against the arm 100 such that the arm does not engage the pin 96 on the cable carrier until a force is exerted and maintained on the lever arm 104. The biasing spring 105 can be connected to the arm 100 and to a hole 107 provided on the housing.

Also provided in the cavity 90 is a ramp 108 which is freely slidable within the cavity. The ramp includes an extending pin 110 which extends outwardly of the housing through a slot 112. The extending pin 110 extends outwardly of the housing through the slot so as to be manually movable within the slot to correspondingly move the ramp. The ramp includes a sloped or inclined leading end which engages the slotted end of the arm 100 to move the slotted arm 100 to engage the slot 98 with the pin 96 on the cable carrier. The ramp serves as a safety in that the staples cannot be fired until the ramp has been moved to engage the slot with the pin in the cable carrier.

The cable carrier 88 includes a recess 114 which is adapted to receive a connecting rod 116. The connecting rod is fastened in the cable carrier. The connecting rod is connected to or forms at its other end a threaded rod 118 which includes threads 124 on its outer surface. The threaded rod 118 and connecting rod 116 fit within the cable carrier and housing such that they do not rotate but move axially (or longitudinally) within the housing in the direction of the indicated arrows along the threaded rod.

A rotatable knob 120 is mated to the housing but freely rotatable with regard to the housing. The rotatable knob includes threads 122 on at least a portion of its inner surface which engage the threads 124 on the threaded rod. The rotatable knob 120 can be connected to the housing through pins 126 which mate with an annular channel on the rotatable knob to hold the rotatable knob on the housing but permit it to freely rotate. Rotation of the rotatable knob causes the threaded rod to move inwardly and outwardly of the handle housing, thereby concomitantly moving the cable carrier and cable. The function of the rotatable knob will be hereinafter described with regard to the overall operation of the flexible stapler instrument assembly.

With regard to FIG. 3, there is shown a staple firing head assembly 14. As can be seen from the drawing, the staple firing head assembly 14 is connected to the handle actuator assembly through the cable 24 or 86, depending on whether the handle actuator assembly is that of FIG. 1 or 2. The staple firing head assembly 14 is basically constructed of three components: a body 128; a cartridge assembly 130; and an anvil assembly 132.

The body 128 includes a fixed pusher 166. The term fixed is used to mean that in a longitudinal reference frame relative to the handle actuator assembly and flexible spine assembly, the pusher 166 remains in a fixed position. The other elements of the body, as well as the cable, cartridge assembly, and anvil assembly do move relative to the pusher. The other elements of the body are an anvil shaft tube 140 slidably mounted within the pusher, and a bayonet member 150 slidably mounted on the anvil shaft tube 140.

The cable 24 extends through the staple firing head assembly and is attached to the anvil assembly by cable retainer 136. The anvil assembly 132 includes an anvil shaft 134 which is generally cylindrical in shape and extends into the body and, more particularly, into the pusher and into a recess 138 on the anvil shaft tube for the anvil shaft. The anvil is removably attached to the anvil shaft so that the staple cartridges can be inserted in the stapling instrument. The anvil shaft 134 is freely slidable within the recess 138 of the anvil shaft tube. That is, the anvil shaft 134 can freely slide within the recess and is biased within the anvil shaft tube by an anvil return spring 142 which is a coiled spring extending around the cable. The anvil return spring in a working embodiment was a helically wound spring having a preload of about 2.5 pounds and a final load of about 5 pounds. The cable extends centrally through the anvil shaft and anvil shaft tube.

The body 128 is generally cylindrical in shape. However, the body can have other configurations such as a multi-sided tubular shape. The anvil shaft 134 is generally cylindrical in shape as is also the anvil shaft tube 140. Again, other tubal configurations can be used.

Extending outwardly from the anvil shaft tube are two bayonet pins 144. The bayonet pins 144 are encircled by a collar 146. The bayonet pins extend through two provided slots 154 on the pusher 166 and through two slots 148 on the bayonet 150. The slots 148 are preferably about 2 millimeters in length and provide for various thicknesses of tissue to be stapled. The function of the slots 148 and bayonet pins 144 will hereinafter be described with regard to the operation of the overall flexible stapling instrument assembly. The anvil shaft tube can slide within the slots 154 and 144 and thereby move relative to the pusher and bayonet.

The anvil shaft tube 140 is also slidable within the pusher 166. That is, the anvil shaft tube 140 rides within a recess 152 for such anvil shaft tube, which recess is within the pusher 166. The bayonet is also freely slidable concomitantly with the anvil shaft tube 140. The bayonet and anvil shaft tube move relative to the pusher 166. The bayonet 150 is a generally cylindrical shape and includes a forward cylindrical extension designed to receive the cartridge assembly 130.

Extending around the pusher 166 is a tissue clamping compression spring 156. The tissue clamping spring 156 is fixed between a ledge 162 on the bayonet 150 and the bayonet pins 144 on the anvil shaft tube (via the collar 146). The tissue clamping spring biases the bayonet against the anvil shaft tube. In a working embodiment, the tissue clamping spring was a spring having a preload of about 5 pounds and a final load of about 9 pounds.

Also extending around the pusher 166 is a firing spring 158 which is a helically wound compression spring. In a working embodiment, the firing spring had a preload of about 16 pounds and a final load of about 23 pounds. The firing spring is biased between the bayonet pins 144 of the anvil shaft tube (via the collar 146) and an end cap 160 attached to the pusher 166. The end cap 160 includes a concave hemispherically-shaped recess 164 adapted to mate with the hemispherical forward surface of a spine segment.

The pusher 166 includes a forwardly extending cylindrical end which is designed to engage the staple drivers within the cartridge assembly. The bayonet 150 forms a cylindrical cavity or recess 168 for receiving the cartridge assembly 130. The flexible stapling instrument assembly herein has been designed for use with various commericially available staple carrying cartridge assemblies. The commercially available cartridge assemblies can be used in the instrument assembly herein. In particular, cartridge assemblies manufactured by U.S. Surgical Corporation, can be used in the instrument assembly herein. Suitable cartridge assemblies are described in U.S. Pat. No. 4,304,236, the entire disclosure of which is incorporated herein by this reference. The cartridge assembly will be described herein in order to disclose the operation of the overall flexible stapling instrument assembly.

The typical cartridge assembly includes a cylindrical projection 170 which fits into the recess 168 on the bayonet. The cartridge assembly also includes a staple driver 172 which includes a plurality of integral individual drivers 174 which coincide and fit into staple receiving slots 178 wherein the staples 176 are located. There is one staple for each slot. Centrally located within the cartridge assembly is a cylindrical-shaped knife blade 180. The knife blade is movable in the cartridge and is moved by movement of the staple driver 172 as it also drives the staples. In the cartridge assembly shown in FIG. 3, the staples form two concentric circular patterns wherein the staples in one of the circular patterns overlap the gaps between staples in the other circular staple pattern. Coinciding with the staples in the cartridge assembly are a series of depressions 182 on the anvil surface of the anvil assembly 132.

Figure 5:
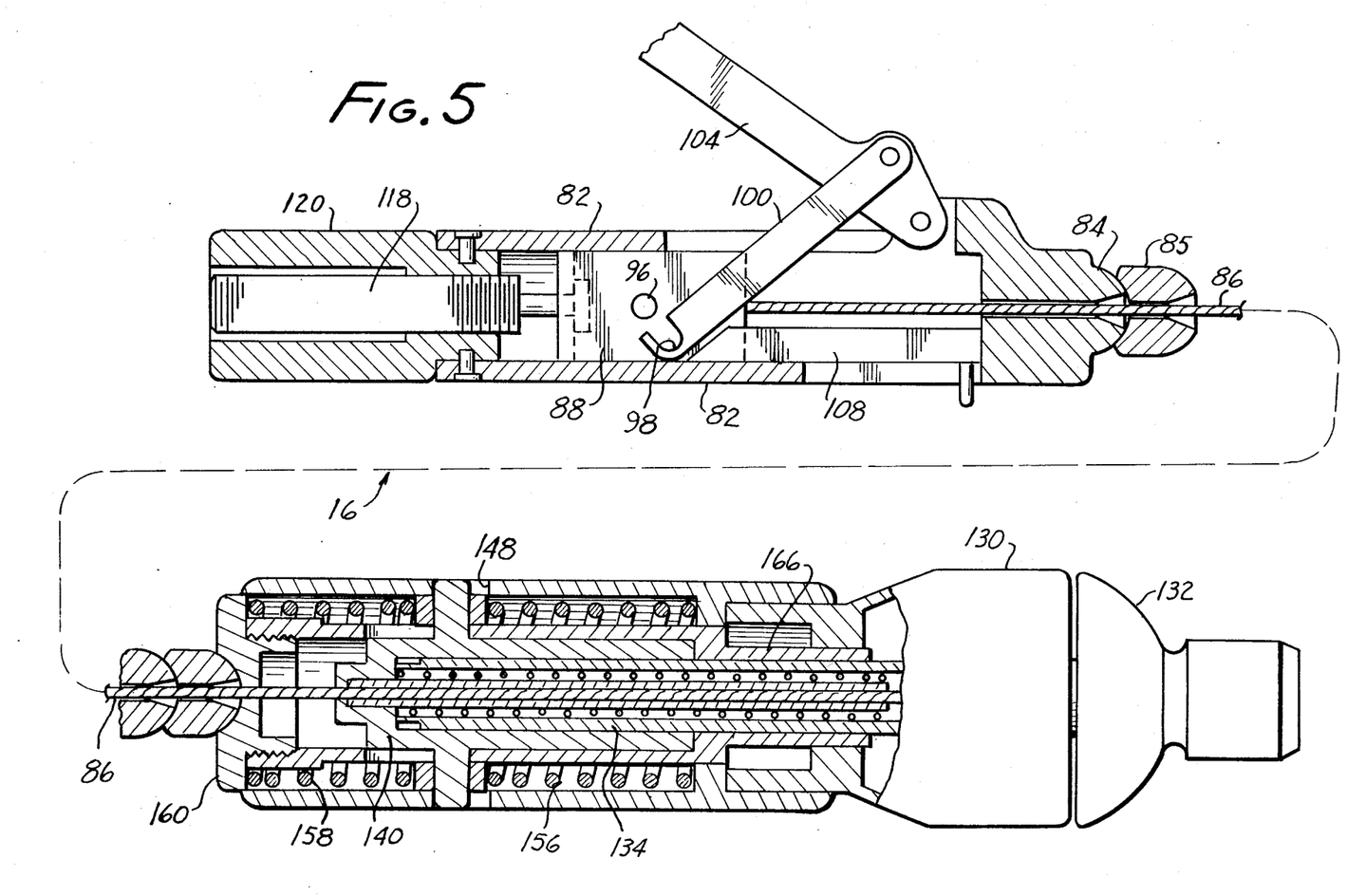
FIG. 5 is a side elevational view partially in cross section of the assembly in FIG. 4 illustrating the assembly during the approximation of tissue between the anvil and staple housing.
Figures 6, 7:
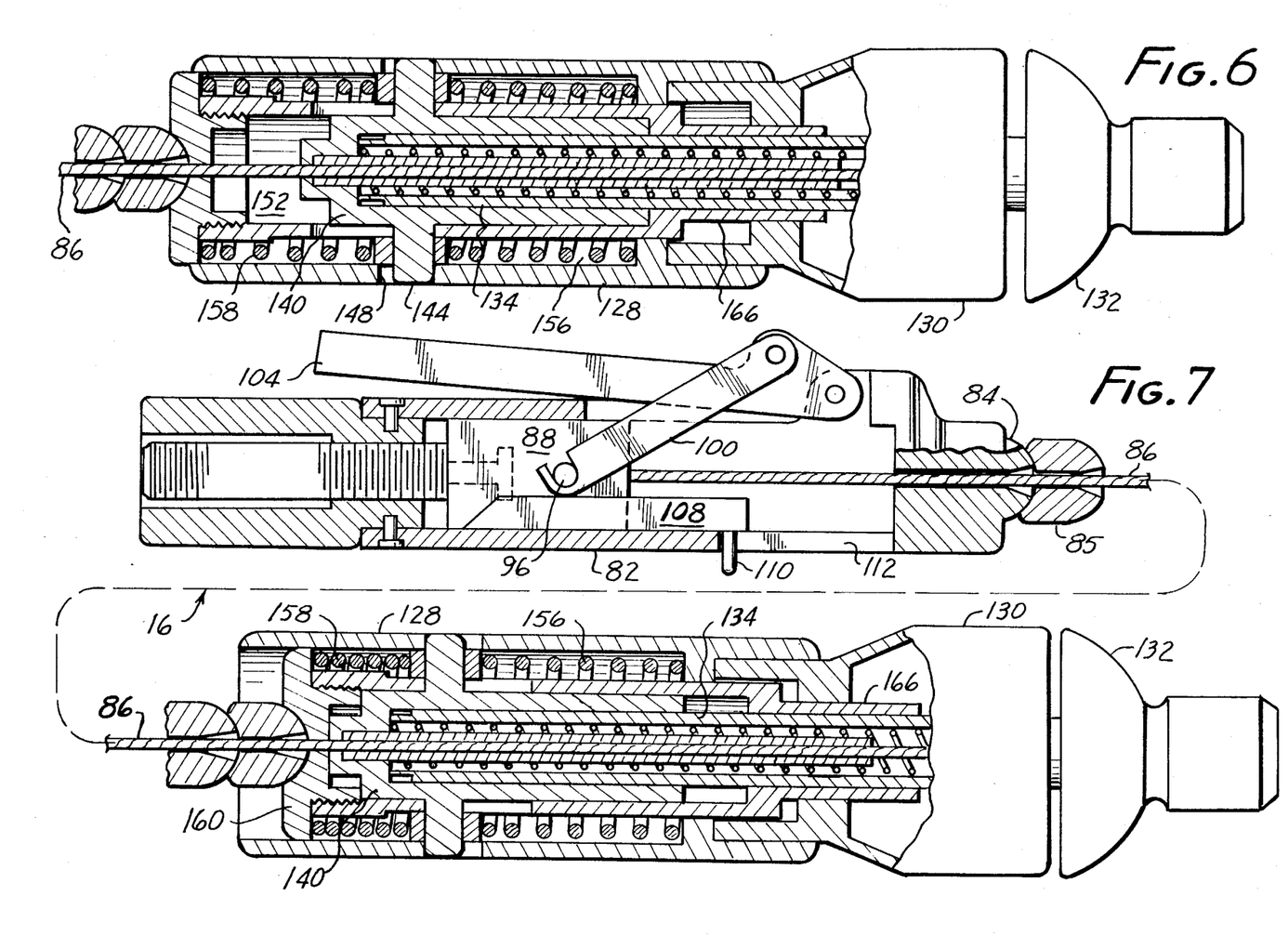
FIG. 6 is a side elevational view partially in cross section of the staple firing head assembly of FIG. 4 showing the approximation of a thicker tissue in the staple firing head assembly.
FIG. 7 is a side elevational view partially in cross section illustrating the assembly shown in FIG. 4 upon firing of the staples therein.

The operation of the flexible stapler instrument assembly herein will be described with regard to the assembly shown in FIGS. 4–7. The flexible stapling instrument assembly shown in FIG. 4 is an illustration of the assembly at rest and prior to use. The assembly shown in FIG. 5 illustrates the approximation of tissue and the assembly illustrated in FIG. 6 illustrates the approximation of a thicker tissue. The assembly illustrated in FIG. 7 shows the assembly during the firing or immediately after the firing of the staples; i.e., the forming of the staples against the anvil surface. With regard to the following description of the assembly shown in FIGS. 4–7, the term "rearward" shall be used with reference to the handle actuator assembly end of the overall assembly while the term "forward" will be used with reference to the staple firing head assembly end of the overall assembly.

In FIG. 4, the flexible stapling instrument assembly 10 is shown which includes a handle actuator assembly 12, a staple firing head assembly 14, and a flexible spine assembly 16 joining the handle actuator assembly and the staple firing head assembly. The flexible stapler instrument assembly 10 is shown in FIG. 4 in its ready to use position. The anvil assembly is usually drawn toward the staple housing before insertion into the tissue prior to clamping the tissue to be stapled. The gap in FIG. 4 is shown somewhat exaggerated.

In the flexible stapler instrument assembly 10, and more particularly the stapling head assembly 14, the anvil assembly 132 is spaced from the staple cartridge 130 a distance sufficient to enable the two tubular sections to be lapped over the opposing faces on the staple cartridge and the anvil assembly. The anvil return spring 142 is in its extended position holding the anvil assembly spaced from the staple cartridge 130. The anvil shaft 134 is at the forward end of the anvil shaft tube 140, leaving the recess 138 for receiving the anvil shaft in the anvil shaft tube. The tissue clamping spring 156 is in its extended state holding the anvil shaft tube 140 in a position such that the bayonet pins 144 are positioned at the rearward end of the slot 148 in the body 128. The anvil shaft tube 140 is positioned within the pusher 166 such that a recess 152 remains between the end cap of the pusher and the rearward end of the anvil shaft tube.

With regard to the handle actuator assembly, the cable carrier 88 lies within the cavity of the handle actuator assembly 12 toward the forward end of such cavity; i.e., toward the front spacer 84. The threaded rod 118 which is connected to the cable carrier is positioned such that it extends into the cavity and only a relatively small portion extends toward the rotatable knob 120.

The lever assembly is positioned with the arm 100 disengaged from the extending pin 96 on the cable carrier and the spring tension on the lever 104 is such that the lever projects outwardly from the housing 82. The ramp 108 is positioned toward the forward end of the cavity such that the pin 110 is at the forward end of the slot 112. The ramp, thus, does not engage the arm 100.

FIG. 5 illustrates a later position for the flexible stapler instrument assembly shown in FIG. 4 at a stage wherein tissue is being approximated. That is, the tissue of the organs to be joined end to end would not be clamped between the anvil assembly 132 and the staple cartridge 130. In order to clamp the tissue, the rotatable knob 120 is rotated to engage the threaded rod 118 and to cause the threaded rod 118 to move rearwardly in the handle actuator assembly. The rotatable knob 120 rotates but does not move inward or outward with regard to the housing 82. The threaded shaft 118 does not rotate but moves rearwardly or forwardly, depending upon the rotation of the rotatable knob 120. As the rotatable knob is rotated, it draws the threaded rod 118 rearwardly and concomitantly pulls the cable carrier 88 rearwardly of the cavity 90 within the housing 82.

As the cable carrier 88 has been drawn rearward by the threaded rod 118, it also draws the cable 86 rearward through the housing 82, the flexible spine assembly 16 (through its individual spine segments 85), and through the pusher 166, and draws the anvil assembly 132 toward the staple cartridge 130. As can be seen in FIG. 5, the anvil assembly 132 is spaced closely to the staple cartridge 130. In a normal stapling operation, the anvil would be spaced approximately 1 millimeter from the staple cartridge for normal thicknesses of tissue. The staple firing head assembly has also changed positions with regard to the individual element positions in FIG. 4. As can be seen in FIG. 5, the anvil shaft 134 has now compressed the anvil return spring and has filled the recess 138 within the anvil shaft tube 140. The tissue clamping spring 156 maintains the anvil shaft tube 140 positioned such that the bayonet pins 144 remain at the rearward end of the slot 148. In FIG. 5, compression of the firing spring 158 has not yet begun.

It should also be noted that in FIG. 5 the cable carrier 88 is properly positioned within the cavity 90 of the housing 82 such that the extending pin 96 can be engaged with the slot 98 on arm 100 of the trigger assembly. Ramp 108 remains in the position shown in FIG. 4 at the forward end of the cavity 90 in the housing.

FIG. 6 shows an alternative arrangement for the elements of the staple firing head assembly shown in FIG. 5 when the handle actuator assembly is in the position shown in FIG. 5. The orientation of the elements in FIG. 6 provides a gap between the anvil assembly 132 and the staple cartridge which is relatively larger than the gap shown in FIG. 5. For example, the configuration shown in FIG. 6 can provide for the approximation of thicker tissues and the spacing can be about 3 millimeters for such thicker tissues.

The anvil shaft 134 has been drawn into the anvil shaft tube 140 filling the recess therein. As the anvil has been drawn rearward, it compresses the tissue and exerts a pressure through such tissues against the staple cartridge 130 which is connected to the bayonet 150. A compressive force is exerted against the tissue clamping spring 156 as the bayonet 150 is pulled rearwardly. The bayonet pins 144 thus engage the forward end of the slot 148 in the bayonet.

The two orientations of the elements of the staple firing head assembly shown in FIGS. 5 and 6 show the approximation of tissue between the anvil and staple cartridge and show the assembly in a condition for firing the staples into the tissue. The sequence of firing and the orientation of the various elements upon firing is shown in FIG. 7. For the various configurations and arrangement of the elements shown in FIGS. 4-6, the anvil assembly, cartridge assembly, and bayonet of the staple firing head assembly have all been pulled rearward by the cable 86 which has been pulled rearward by the rotatable end cap 120 pulling the cable carrier. In order to fire the staples, the ramp 108 must be slid rearwardly by manually sliding the ramp by exerting a force on the pin 110 extending from the housing. The sloped or inclined rearward end of the ramp engages the arm 100 and slides such arm to engage the slot on the end of the arm with the extending pin 96 on the cable carrier as shown in FIG. 7. The ramp 108 functions as a safety and prevents firing of the staples prior to the sliding of the ramp rearward to engage the slot on the arm with the pin.

With reference to FIG. 7, the squeezing of the lever 104 toward the housing of the handle actuator assembly pivots the lever 104 and causes arm 100 to move rearwardly and drive the cable carrier rearwardly. The rearward movement of the cable carrier pulls the cable 86 through the housing, through the flexible spine assembly to fire the staples. The firing of the staples occurs with regard to the staple firing head assembly as the anvil assembly to which the cable is attached is drawn rearward and concomitantly pulls the staple housing rearward. The anvil shaft tube and bayonet also move rearward with respect to the staple pusher 166. The staple pusher 166 is maintained in a fixed position relative to the cable 86 by the exertion of a stationary retaining force through the spine segments which are connected to the pusher assembly at the rearward end cap 160. As the staple cartridge 130 moves rearward, it encounters the forward cylindrical projection on the pusher 166 which pushes against the staple drivers. The staple drivers and staples thus remain in a fixed position as the staple housing moves rearward away from the staples. The anvil surface, along with its depressions, moves toward the staples for forming the staples. The anvil shaft tube is pulled against the firing spring 158 which sits between the pusher and the anvil shaft tube.

In FIG. 5, the anvil shaft has bottomed out against the anvil shaft tube which correspondingly transmits the cable load to the bayonet pins 144 and the bayonet 150, causing the staple cartridge 130 to move together with the anvil assembly rearwards. In FIG. 6, the anvil shaft has also bottomed out against the anvil shaft tube, but the staple cartridge 130 and bayonet 150 have been pushed by the thicker tissue rearwards relative to the anvil shaft tube 140 and bayonet pins 144, causing the tissue compression spring 156 to deflect and the bayonet pins 144 to be at the forward end of slots 148.

To fire the staples in a working embodiment, the cable carrier is moved rearwardly about one-quarter to about three-eighths of an inch by actuation of the lever 104 and arm 100. Before clamping tissue, the initial gap between the anvil surface and the staple cartridge in a working embodiment is approximately one and three-quarter inches as shown in FIG. 4.

In regard to FIG. 8, another type of staple firing head assembly is illustrated. The staple firing head assembly 15 shown in FIG. 8 provides a linear staple pattern and generally such an instrument does not include a knife blade. The staple firing head assembly 15 in FIG. 8 includes a body 184 which is generally cylindrical in shape and hollow defining a cavity 194. The cable 24 or 86 (depending on the choice of handle actuator assembly) extends through the body. The body includes an end cap 29 having a hemispherical recess for receiving the hemispherically-shaped spine segment 78.

The staple firing head assembly 15 includes an anvil carrier 188 which includes an anvil 186. The anvil 186 provides an anvil surface consisting of a plurality of staple forming depressions or grooves. The anvil carrier is somewhat C-shaped and includes an anvil carrier shaft 192 which is generally cylindrical tubular shaped and which fits into and is received in the cavity 194 of the body of the staple firing head assembly. The anvil carrier shaft and thereby the anvil carrier are slidingly engaged with the cavity 194 of the body and is free to slide within such cavity.

The anvil carrier includes an anvil carrier end cap 190 on the rearward end of the anvil carrier shaft. The anvil carrier end cap is adapted to receive and connect with a fitting on the end of the cable 24. The anvil carrier shaft 192 is hollow and defines a cavity 204 which slidingly receives a cartridge holder shaft 202.

The staple firing head assembly includes a cartridge holder 198 which provides an opposing surface on which a staple cartridge can be inserted opposite the anvil surface. The cartridge holder 198 is adapted to receive a cartridge 196 which contains the staples to be fired. The cartridge holder 198 includes the cartridge holder shaft 202 which extends into the cavity 204 of the anvil carrier shaft. The cartridge holder shaft 202 is spring biased against the anvil carrier by an anvil return spring 208. The anvil return spring can be a helically wound compression spring which extends around the cartridge holder shaft and engages a ledge 212 at the rearward end thereof. The forward end of the anvil return spring engages the anvil carrier. The anvil return spring can have a preload of about 2 pounds and a final load of about 5 pounds and a spring force of about 5 pounds per inch.

The cartridge holder 198 includes a pusher head 206. The pusher head is designed to apply a force against the staple drivers, forcing the staple drivers against the staples and the staples from the staple recesses and against the staple forming grooves on the anvil surface. The pusher head 206 is part of the pusher assembly 200 which includes a shaft that is attached to the body 184. Thus, the pusher assembly 200 does not move relative to the body 184 which is abutted against the spine segments so the the body 184 does not move relative to the handle actuator assembly. That is, the cable moves relative to the body 184 and pusher assembly.

Extending around the pusher shaft is a staple firing spring 210. The staple firing spring provides a spring bias between the cartridge holder/anvil carrier and the housing. The staple firing spring can have a preload of about 7.5 pounds and a final load of about 11.5 pounds and a spring force of about 13.5 pounds per inch.

The staple firing head assembly 15 shown in FIG. 8 represents the staple firing head assembly at its rest or normal position prior to use. In such a position, it would be connected to a handle actuator assembly which would be in the configuration of the handle actuator assembly shown in FIG. 4.

FIG. 9 represents the staple firing head assembly 15 shown in FIG. 8 while in use and showing the approximation of tissue between the anvil surface and staple cartridge. In such a state shown in FIG. 9, the handle actuator assembly would be in the position as the handle actuator assembly shown in FIG. 5. That is, the rotatable knob would be turned to draw the cable carrier and cable through the housing of the handle actuator assembly. As the cable is drawn through the handle actuator assembly, it is also drawn through the flexible spine 16 and through the housing body 184 of the staple firing head assembly. The cable is attached to the anvil carrier and draws the anvil carrier and anvil surface toward the staple cartridge. As the anvil carrier is drawn rearwardly by the cable, it compresses the anvil return spring 208. The anvil carrier shaft 192 is drawn into the cavity 194 on the body 184.

The staple firing head assembly 15 shown in FIG. 10 represents the assembly upon firing or forming of the staples. In the configuration shown in FIG. 10, the handle actuator assembly would be positioned the same as the handle actuator assembly shown in FIG. 7. That is, in the handle actuator assembly the slotted arm 100 would be engaged with the pin on the cable carrier and, upon actuation of the lever 104, the arm 100 would force the cable carrier rearward, thereby pulling the cable rearward. With the pulling of the cable rearward, there would be a corresponding pulling of the cable through the staple firing head assembly 15 which would pull the anvil carrier shaft toward the rearward end of the cavity 194 and the body 184. The anvil carrier shaft would be pulled against the firing spring 210. As the anvil carrier is pulled against the firing spring 210, the spring would exert a force against the pusher shaft 202 to resist movement of such pusher shaft by the spring force. The firing spring 210 is also biased against the body 184 which does not move relative to the moving cable. As the cable is pulled rearward, the pusher shaft 202 pulls the cartridge holder 198 rearwardly past the pusher head 206. As the cartridge holder and cartridge continue to move rearward, the staples are forced outwardly of the cartridge by the pusher head and against the grooves in the anvil surface whereby they are formed.

The flexible stapler instrument herein provides benefits in that the assembly can be adapted for use with varying staple firing head assemblies as discussed above. In addition, the flexible stapling instrument assembly herein provides adaptability for use in stapling various tissues as the staple firing head assembly can be readily positioned due to the flexible spine linking the staple firing head assembly to the handle actuator assembly. The flexible surgical stapling instrument herein provides an instrument which basically has a single moving cable that pulls the anvil toward the staples and subsequently pulls the staple cartridge assembly past the staples which are held in a fixed position. The staples then encounter the approaching anvil surface and its corresponding grooves which, as it continues to move toward the staples, forms the staples through the tissue clamped between the anvil surface and the staple cartridge.

The flexible stapler instrument herein also provides a surgical stapling assembly which can be provided in component parts. That is, the flexible stapler instrument herein can be constructed such that the handle actuator assembly can be constructed of reusable materials to provide a reusability for the handle actuator assembly. The staple firing head assembly and the flexible spine assembly can be constructed of materials that make such assemblies disposable. The staple firing head assembly and flexible spine assembly can be constructed of plastic or include some plastic parts, or can be constructed rather inexpensively to provide disposability. It is an advantage of the overall assembly that the staple firing head assembly and flexible spine assembly can be disposable. The staple firing head assembly and flexible spine assembly comprise the two components of the overall assembly herein which are inserted into the body of the patient. By constructing these two assemblies such that they are disposable, the inherent problems associated with reusing surgical instruments can be avoided. Namely, the problems of cross-contamination, sterilization, and associated staff time to disassemble, sterilize, and reassemble can be avoided. Another problem that is avoided by making the staple firing head and flexible spine assembly disposable or for use on individual patients is that cable stretch over time is avoided. Cable stretch can occur when the same cable is used repeatedly.

Another feature of the present invention is the ability to provide a handle actuator assembly which can be used with a variety of staple firing head assemblies and flexible spine assemblies. Such a feature is desirable as different lengths of flexible spine assemblies can be used and fitted to the handle actuator assembly. That is, if a particular procedure calls for a particular length of flexible spine assembly, then a staple firing head assembly having the appropriate length of flexible spine assembly can be interconnected to a reusable handle actuator assembly. The flexible stapler instrument assembly herein is advantageous in that it can be used to reduce hospital costs in that the handle actuator assembly can be reusable and the staple firing head assembly and flexible spine assembly can be disposable. In addition, the handle actuator assembly can be used with a variety of staple firing heads such as those shown in the accompanying drawings, depending upon the type of staple pattern to be used.

Without the flexible spine segments the assembly herein can be operated with two hands. One hand can hold the staple firing head assembly in position and the other, or second hand, can operate the handle actuator assembly. In such a two-handed operation the first hand holds the staple firing head assembly in a fixed position relative to the cable, that is at the same distance from the handle actuator assembly. However, it is preferred to use the spine segments as they permit one hand operation of the assembly.

It should also be appreciated that the surgical stapling instrument assembly herein can be constructed without providing flexibility between the handle actuator assembly and staple firing head assembly. In such an assembly the cable can be replaced with a length of tubing or a rod and the spine segments encircling the cable can be replaced with a length of tubing through which the rod can extend. The operation of the stapling instrument assembly would remain the same with the respective elements of both the handle actuator assembly and staple firing head assembly moving relative to one another as earlier described herein with regard to the preferred flexible surgical stapling instrument assemblies.

We claim:

1. A handle actuator assembly for use with a flexible surgical stapling instrument, the handle actuator assembly comprising:
   a housing defining an inner cavity therein;
   a cable carrier movable within the cavity including cable connection means for connecting the cable carrier means to a length of flexible cable;
   a pin extending from the cable carrier;
   a first lever arm pivotally attached to the housing;
   a second lever arm pivotally attached to the first lever arm and a slot on the second lever arm wherein the second lever arm is cooperatively attachable through such slot to the extending pin of the cable carrier; and
   tissue approximation means on the housing operataively connected to the cable carrier for selectively adjusting the position of the cable carrier within the cavity; and
   ramp means in the housing cooperatively engageable with the second lever arm to engage the slot on the second lever arm with the extending pin on the cable carrier.

2. A kit for use in a procedure for sugically stapling tissue, the kit comprising:
   a handle actuator assembly comprising:
      a housing defining an inner cavity therein;
      a cable carrier slidable within the cavity and including cable connection means for connecting the cable carrier to a length of flexible cable; and
      a handle means on the housing selectively operatively connected to the cable carrier;
   a staple firing head assembly comprising:
      an anvil assembly means including and anvil surface, which anvil surface includes an array of staple forming depressions and including cable connection means for connecting the anvil assembly means to a length of flexible cable;
      a staple housing means for carrying an array of staples; and a staple pusher means for exerting a force on staples in the staple housing means to eject the staples from the staple housing means and form the staples against the anvil surface; and a length of flexible cable capable of being connected at one of its ends to the cable carrier in the handle actuator assembly and at its other end to the anvil assembly means of the staple firing head assembly, which length of flexible cable extends at least along a portion of its length through a plurality of spine segment means for maintaining the staple pusher means in a fixed position along the length of flexible cable relative to the handle actuator assembly when the handle actuator assembly, length of flexible cable and staple firing head assembly are operatively interconnected.

3. A surgical stapling instrument assembly comprising:
 a staple firing head assembly comprising:
 a staple cartridge receiving means for receiving a staple cartridge carrying an array of staples and staple drivers for such staples;
 an anvil assembly means including an anvil surface, which anvil surface includes an array of staple forming depressions;
 an anvil shaft on the anvil assembly means; and
 staple pusher means for contacting the staple drivers in the staple cartridge to force the staple drivers against the staples and the staples subsequently against the anvil surface as the staple cartridge receiving means, anvil assembly means, and anvil shaft move with respect to the staple pusher means;
 a handle actuator assembly comprising:
 a housing defining an inner cavity therein;
 a carrier bolt movable within the cavity therein;
 connecting means attached to the carrier bolt and to the anvil assembly means for imparting movement to the anvil assembly means when the carrier bolt is moved;
 a first lever arm pivotally attached to the housing;
 a second lever arm pivotally attached to the first lever arm and cooperatively attachable to the carrier bolt; and
 tissue approximation means on the housing operatively connected to the carrier bolt for selectively adjusting the position of the carrier bolt within the cavity; and
 static means extending between the housing of the handle actuator assembly and the staple pusher means of the staple firing head assembly for maintaining the staple pusher means in a fixed position with regard to movement toward the housing of the handle actuator assembly along the connecting means when the carrier bolt, connecting means, and anvil assembly means move.

4. An assembly as recited in claim 3 wherein the connecting means comprises a length of flexible cable.

5. An assembly as recited in claim 4 wherein the static means comprises a flexible outer sheath extending around the length of flexible cable.

6. An assembly as recited in claim 5 wherein the static means comprises a plurality of intersecting spine segments, wherein each spine segment includes a hemispherical-shaped end and a hemispherical concave end and the adjacent spine segments are mated with a hemispherical-shaped end being received in the hemispherical concave end of adjacent spine segments.

7. A staple firing head assembly adapted for use with a flexible surgical stapling instrument, the staple firing head assembly comprising:
 a staple cartridge receiving means for receiving a cartridge carrying an array of staples and staple drivers for such staples;
 an anvil assembly means including an anvil surface and an array of staple forming depressing on such anvil surface for forming staples;
 an anvil shaft on the anvil assembly means; and
 staple pusher means rearwardly of the staple cartridge receiving means for contacting the staple drivers to force the staple drivers against the staples in a cartridge and the staples subsequently against the staple forming depressions on the anvil surface as the staple cartridge receiving means, anvil assembly means, and anvil shaft move rearward toward the staple pusher means.

8. An assembly as recited in claim 7 further comprising a length of flexible cable connected at one of its ends to the anvil assembly means.

9. An assembly as recited in claim 8 wherein the length of flexible cable extends through the staple cartridge, staple cartridge receiving means and through the staple pusher means of the staple firing head assembly.

10. An assembly as recited in claim 7 further comprising a first spring biasing means for biasing the anvil assembly means against the staple cartridge receiving means and second spring biasing means for biasing the staple cartridge receiving means and anvil assembly means against the staple pusher means.

11. An assembly as recited in claim 10 further comprising an anvil shaft receiver means for selectively adjusting the spacing between the anvil surface and the staple cartridge, which anvil shaft receiver means is slidingly connected to the staple pusher means and adapted to slidingly receive the anvil shaft.

12. An assembly as recited in claim 11 wherein the first spring biasing means comprises a first spring for biasing the anvil shaft receiver means against the staple cartridge receiving means and a second spring for biasing the anvil assembly means against the anvil shaft receiver means, and wherein the second spring biasing means biases the anvil assembly means, anvil shaft receiver means, and staple cartridge receiving means against the staple pusher means.

13. A flexible surgical stapler assembly comprising:
 a staple firing head assembly comprising:
 an anvil assembly means providing an anvil surface, which anvil surface includes an array of staple forming depressions;
 a staple housing means for carrying an array of staples;
 an array of staples in the staple housing means; and
 a staple pusher means for exerting a force on the staples in the staple housing means to eject the staples from the staple housing means and form the staples against the anvil surface;
 a handle actuator assembly comprising:
 a housing defining an inner cavity therein;
 a cable carrier slidable within the cavity;
 a length of flexible cable connected at one of its ends to the cable carrier and at its other end to the anvil assembly means of the staple firing head assembly; and
 a handle means on the housing selectively operatively connected to the cable carrier for moving the cable carrier and concomitantly forcing the staples out of the staple housing means and forming the staples against the anvil surface; and static means extending between the handle actuator assembly and staple firing head assembly for maintaining the staple pusher means in a fixed position with regard to movement toward the handle actuator along the length of flexible cable when the anvil assembly means, length of flexible cable, and staple housing means move toward the handle actuator assembly.

14. An assembly as recited in claim 13 wherein the static means comprises a plurality of individual interconnecting cylindrical spine segments each having hemispherically-shaped concave and convex ends and a centrally extending lumen through which the cable extends.

15. An assembly as recited in claim 13 wherein the staple firing head assembly further comprises:
an anvil shaft on the anvil assembly means slidingly engaged with the staple pusher means;
a first spring biasing means for biasing the anvil assembly means against the staple housing means; and
a second spring biasing means for biasing the staple housing means against the staple pusher means.

16. An assembly as recited in claim 15 further comprising:
an anvil shaft receiver means slidingly mounted with respect to the staple pusher means and which is adapted to slidingly receive the anvil shaft; and
wherein the first spring biasing means comprises a first spring biasing the anvil assembly means against the anvil shaft receiver means and a second spring biasing the anvil shaft receiver means against the staple housing means and wherein the second spring biasing means biases the anvil shaft receiver means and staple housing means against the staple pusher means.

17. An assembly as recited in claim 13 wherein the cable carrier further comprises connecting means for selectively connecting the handle means to the cable carrier.

18. An assembly as recited in claim 17 wherein the connecting means on the cable carrier comprises an extending pin for engaging the handle means.

19. An assembly as recited in claim 18 wherein the handle means comprises a first lever arm pivotally attached to the housing and a second lever arm pivotally attached to the first lever arm and selectively attachable to the cable carrier.

20. An assembly as recited in claim 19 wherein the second lever arm includes a slot which can be engaged with the extending pin on the cable carrier.

21. An assembly as recited in claim 20 further comprising ramp means in the housing cooperatively engageable with the handle means and cable carrier to engage the slot on the second lever arm of the handle means with the extending pin on the cable carrier.

22. An assembly as recited in claim 13 further comprising tissue gap adjustment means on the handle actuator assembly and operatively connected to the cable carrier for selectively adjusting the distance between the anvil surface and staple housing means.

23. An assembly as recited in claim 22 wherein the tissue gap adjustment means comprises a rotatable knob rotatingly connected to the housing of the handle actuator assembly and operatively connected to the cable carrier such that rotation of the rotatable knob moves the cable carrier and cable and concomitantly moves the anvil assembly means toward the staple housing means.

24. An assembly as recited in claim 22 wherein the tissue gap adjustment means comprises a rotatable knob keyed to the housing of the handle actuator assembly and including a centrally, axially extending threaded lumen and a threaded rod in the threaded lumen, which threaded rod is connected to the cable carrier, whereby the threaded rod does not rotate but moves axially of the threaded lumen, such that rotation of the rotatable knob moves the threaded rod, cable carrier and cable and concomitantly moves the anvil assembly means toward the staple housing means.

25. An assembly as recited in claim 13 wherein the staple firing head assembly further comprises:
an anvil shaft on the anvil assembly means, which anvil shaft is slidingly connected to the staple pusher means; and
wherein the staple housing means is slidingly connected to the staple pusher means such that the staple housing means moves relative to the staple pusher means a distance sufficient to eject staples from the staple housing means and form the staples against the anvil surface.

26. An assembly as recited in claim 25 further comprising a first spring biasing means for biasing the anvil assembly means against the staple housing means and second spring biasing means for biasing the staple housing means and anvil assembly means against the staple pusher means.

27. An assembly as recited in claim 26 wherein the first spring biasing means comprises a lesser spring force than the spring force for the second spring biasing means.

28. An assembly as recited in claim 27 wherein the spring force of the first spring biasing means comprises a spring force relative to the spring force of the second spring biasing means such that the anvil assembly means moves relative to the staple housing means, and upon overcoming the first spring biasing means, the anvil assembly means and staple housing means move relative to the staple pusher means against such second spring biasing means.

29. An assembly as recited in claim 26 further comprising an anvil shaft receiver means for selectively adjusting the spacing between the anvil surface and staple housing means, which anvil shaft receiver means is slidingly connected to the staple pusher means and adapted to slidingly receive the anvil shaft.

30. An assembly as recited in claim 29 further comprising a third spring biasing means for biasing the anvil shaft receiver means against the staple housing means and wherein the first spring biasing means biases the anvil assembly means against the anvil shaft receiver means and wherein the second spring biasing means biases the anvil assembly means, anvil shaft receiver means, and staple housing means against the staple pusher means.

31. An assembly as recited in claim 30 wherein the first spring biasing means comprises a spring force less than the spring force of the third biasing means, which third biasing means comprises a spring force less than the spring force of the second spring biasing means.

32. An assembly as recited in claim 31 wherein the relative spring forces of the first, second, and third spring biasing means are such that the anvil assembly means moves relative to the anvil shaft receiver means until the first spring biasing means is overcome, then the anvil assembly means and staple housing means move relative to the staple pusher means until the third spring biasing means is overcome, and then the anvil assembly means, staple housing means, and anvil shaft receiver means move relative to the staple pusher means against the second spring biasing means.

* * * * *